United States Patent [19]
Rubin

[11] Patent Number: 4,584,320
[45] Date of Patent: Apr. 22, 1986

[54] ANTI-ASTHMATIC COMPOSITION AND METHOD USING 8,11,14,17-EICOSATETRAENOIC ACID

[76] Inventor: David Rubin, 5 Rav Zair, Jerusalem, Israel

[21] Appl. No.: 688,521

[22] Filed: Jan. 3, 1985

[51] Int. Cl.$^4$ .............................................. A61K 31/20
[52] U.S. Cl. ...................................... 514/560; 514/826
[58] Field of Search ......................................... 514/560

[56] References Cited

U.S. PATENT DOCUMENTS 4,377,526  3/1983  Fujita et al. ......................... 260/424

OTHER PUBLICATIONS

Chemical Abstracts 85: 137703f, (1976).
Burka, J. F. et al. "Effects of Modulators of Arachidonic Acid Metabolism of the Synthesis and Release of Slow-Reacting Substance of Anaphylaxis" Br. J. Pharmac. 65, pp. 35–41, (1979).
Hitchcock, M. et al., "Arachionic Acid Metabolism and Modulation of in vitro Anaphylaxis by 5, 8, 11, 14--eicosatetraynoic Acid and 9a,12a-Octadecadiynoic Acid", Br. J. Pharmac., 72, 689–695, (1981).
Yecies, L. D. et al., "Slow Reacting Substance (SRS) From Ionophore A23187-Stimulated Peritoneal Mast Cells of the Normal Rat", The Journal of Immunology, vol. 122, No. 5, pp. 2090–2095, (1979).
Crawford, M. A., "Background to Essential Fatty Acids and Their Prostanoid Derivatives", British Medical Bulletin, vol. 39, No. 3, pp. 210–213, (1983).
Higgs, G. A. et al., "Inhibition of Cyclo-Oxygenase and Lipoxygenase", British Medical Bulletin vol. 39, No. 3, pp. 265–270, (1983).
Taylor, G. W. et al., "Lipoxygenase Pathways", British Medical Bulletin, vol. 39, No. 3, pp. 219–222 (1983).
Jakschik, B. A. et al., "Fatty Acid Structural Requirements for Leukotriene Biosynthesis", Prostaglandins, vol. 20, No. 2, pp. 401–410, (1980).
Cohen, N. et al., "Analogs of Atachionic Acid Methylated at C-7 and C-10 as Inhibitors of Leukotriene Biosynthesis", Prostaglandins, vol. 27, No. 4, pp. 553–562, (1984).
Blackwell, G. J. et al., "1-Phenyl-3-Pyrazolidone: an Inhibitor of Cyclo-Oxygenase and Lipoxygenase Pathways in Lung and Platelets" Prostaglandins, vol. 16, No. 3, pp. 417–425, (1978).
Paterson, N. A. M., et al., "Release of Slow-Reacting Substance of Anaphylaxis from Dispersed Pig Lung Cells: Effect of Cyclo-Oxygenase and Lipoxygenase Inhibitors", J. Allergy Clin. Immunol. vol. 67, No. 6, pp. 425–434, (1981).
Nijkamp, F. P. et al., "Leukotrienes, Allergy and Inflammation", Pharmaceutisch Weekblad Scientific Edition, vol. 4, pp. 165–171, (1982).
Sirois, P. et al., "Les Leucotrienes", La Semaine des Hopitaux Paris No. 14, pp. 979–985, (1984).

Primary Examiner—Leonard Schenkman
Attorney, Agent, or Firm—Browdy and Neimark

[57] ABSTRACT

A method for the treatment of asthma, nasal congestion and anaphylactic shock involves nasal or oral administration of 8,11,14,17-eicosatetraenoic acid. Pharmaceutical compositions for this purpose are prepared containing 8,11,14,17-eicosatetraenoic acid and pharmaceutically acceptable vehicles, as well as, preferably, a suitable anti-oxidant.

13 Claims, No Drawings

ANTI-ASTHMATIC COMPOSITION AND METHOD USING 8,11,14,17-EICOSATETRAENOIC ACID

FIELD OF THE INVENTION

The present invention relates to a method for the prevention of asthmatic attacks and bronchial spasms and a composition for use therewith and, more particularly, to such a method and composition which uses a natural compound which can effect inhibition of the biosynthesis of the slow reacting substance of anaphylaxis (SRS-A).

BACKGROUND OF THE INVENTION

It is known that the slow reacting substance of anaphylaxis (SRS-A) is a mediator which is involved in allergic bronchiospasm (asthma) in man. It has been established that SRS-A is produced in the body by metabolism of arachidonic acid (C20:4ω6).

The alternate designations for fatty acids used throughout the present specification, such as C20:4ω6, refer to the total number of carbon atoms in the chain, before the colon; the number of unsaturated bonds, after the colon; and the number of carbon atoms from the end opposite the carboxylic acid at which the first unsaturation appears, following the omega. Members of a given omega series of fatty acids, e.g. ω3 can usually be converted to acids of differing lengths and total number of unsaturations by normal bodily enzymes, but it is generally impossible to change a compound from one omega series to another, e.g. ω3 to ω6. This is because bodily enzymes generally cause changes of length and unsaturation to occur starting from the carboxylic acid end of the chain.

Arachidonic acid is stored in the membranes of the body as part of phospholipids. The arachidonic acid is released from such phospholipids by the action of a phospholipase. The production of the phospholipase which causes release of arachidonic acid may be triggered by any of a variety of mechanisms, including physical irritation and hypersensitivity. Once the arachidonic acid is released into the circulation, it may be oxidized by two different pathways. It is either metabolized by cyclo-oxygenase to produce prostaglandins, or by lipoxygenase to generate hydroperoxy derivatives which may be further metabolized to leucotrienes and SRS-A.

It has previously been theorized that SRS-A production can be inhibited by the inhibition of one or more of the enzymes required for its formation. For example, it is known that corticosteroids act to inhibit the phospholipase stage. Thus, the release of arachidonic acid is inhibited causing the inhibition of the production of all of the metabolites of arachidonic acid, including the prostaglandins. Thus, corticosteroids have been used as anti-inflammatories (inhibition of prostaglandins) as well as anti-asthmatics (inhibition of SRS-A). Unfortunately, however, corticosteroids have severe side effects.

Aspirin-like compounds and indomethacin inhibit only the cyclo-oxygenase pathway of arachidonic acid metabolism. Thus, these compounds can do nothing toward the treatment of asthmatic conditions and, in fact, giving aspirin to an asthmatic may provoke an attack because it forces SRS-A production by inhibiting the cyclo-oxygenase pathway of arachidonic acid.

Compounds which inhibit both the cyclo-oxygenase and lipoxygenase pathways for arachidonic acid metabolism can be expected to reduce SRS-A formation, but are also expected to have undesirable side effects due to the inhibition of the cyclo-oxygenase pathway, as for example, the formation of stomach ulcers. Furthermore, substantially non-toxic natural substances which inhibit both cyclo-oxygenase and lipoxygenase are not known.

Another reason why it is undesirable for an anti-asthmatic drug to also inhibit cyclo-oxygenase is because cyclo-oxygenase is involved in the metabolism of $PGE_1$ from dihomo-gamma-linolenic acid (C20:6ω6), which is an important and desirable prostaglandin. $PGE_1$ interferes with the biosynthesis of cholesterol and endothelial cell proliferation.

Furthermore, there are a variety of lipoxygenases which oxidize various points of the arachidonic acid molecule. The lipoxygenase which catalyzes the production of SRS-A is the 5-lipoxygenase, which oxidizes the double bond of the 5-carbon atom of arachidonic acid. It is thus desirable to specifically inhibit 5-lipoxygenase, thus avoiding inhibition of other enzymes which produce products which are not necessarily undesirable.

The best drug for reduction of SRS-A and thereby for treatment of asthmatic attacks and bronchial spasms, would be a specific 5-lipoxygenase inhibitor which does not inhibit cyclo-oxygenase or other lipoxygenases. Preferably, such a compound should be naturally occurring, so as to be as nontoxic as possible.

SUMMARY OF THE INVENTION

It is an object of the present invention to produce a composition having anti-asthmatic properties.

It is another object of the present invention to produce a composition for the treatment of allergic reactions caused by hypersensitivity.

It is yet another object of the present invention to provide such a composition for the treatment of anaphylactic shock.

It is still another object of the present invention to provide such a composition whose active principle is a naturally occurring fatty acid.

It is a further object of the present invention to provide a method for the treatment of asthmatic conditions and allergic conditions caused by hypersensitivity and anaphylactic shock by administering such compositions.

These and other objects of the present invention are obtained by the use of 8,11,14,17-eicosatetraenoic acid, i.e. C20:4ω3 fatty acid.

DETAILED DESCRIPTION OF PREFERRED EMBODIMENTS

Since arachidonic acid is 5,8,11,14-eicosatetraenoic acid, i.e. C20:4ω6, it comes from the ω6 homologous sequence. SRS-A is produced by the oxidation of arachidonic acid at the double bond of the 5-carbon atom, by lipoxygenase. It occurred to the present inventor to use the eicosatetraenoic acid of the ω3 homologous sequence, i.e., C20:4ω3, in order to inhibit the biosynthesis of SRS-A by being a false metabolite. Having no double bond at the 5-carbon atom, it cannot yield SRS-A. Yet, having a structure very similar to arachidonic acid, insofar as chain length and number of double bonds are concerned, it would be expected to fill the active sites of the enzyme and thus compete with and thereby inhibit the activity of the enzyme on true arachidonic acid.

The 8,11,14,17-eicosatetraenoic acid (hereinafter ETA) used in the present invention, is a natural substance to the extent that it is formed in the body as an intermediate in the alpha-linolenic acid metabolic pathway. See Crawford, M. A., "Background to Essential Fatty Acids and Their Prostanoid Derivatives," *British Medical Bulletin*, Vol. 39, No. 3, pp. 210–213 (1983).

ETA may be synthesized by stoichiometric hydrogenation of pure eicosapentaenoic acid (C20:5ω3). Methods for obtaining pure eicosapentaenoic acid are described in prior U.S. application Ser. No. 545,350, filed Oct. 24, 1983, by the present inventor, as well as in U.S. Pat. No. 4,377,526.

Another method for the preparation of the ETA of the present invention would be to start with alpha-linolenic acid (C18:3ω3); subject it to the enzyme $\Delta^6$-desaturase in order to obtain octadecatrienoic acid (C18:4ω3); and subject this to the action of elongase in order to obtain the eicosatetraenoic acid (C20:4ω6).

ETA is active against asthmatic activity not only as a treatment, but also prophylactically. The compound may be in the form of the free acid or in the form of any pharmaceutically acceptable salt or ester thereof. The compound is preferably taken orally, or by direct oral or nasal inhalation, although it may also be administered parenterally in the form of a pharmaceutically acceptable water soluble salt, such as an alkali metal or ammonium salt, preferably the sodium salt.

Since ETA is a polyunsaturated fatty acid, easily subject to oxidation, any pharmaceutical composition containing ETA should also contain a suitable antioxidant. Preferably, an antioxidant should be chosen which may itself have lipoxygenase inhibiting activity so as to obtain any synergistic effects which may be provided thereby, and at least the additive effects thereof.

Antioxidants which are known to have some degree of lipoxygenase inhibiting activity, include 1-phenyl-3-pyrazolidone (phenidone), propyl gallate and the vitamin E's. Also usable in pharmaceutical compositions of the present invention, are the bioflavanoids, such as luteonol and baicalein. Other conventional anti-oxidants conventionally used as food additives with fatty acids, such as butylated hydroxytoluene, butylated hydroxyanisole, tert-butylhydroquinone, ascorbic acid and its oil-soluble esters, gum guaiac, lecithin and combinations thereof may also be used. A particularly useful combination of antioxidants is ascorbyl palmitate with γ-tocopherol. This combination is known to have many times the antioxidizing activity of either ascorbyl palmitate or γ-tocopherol alone.

Other excipients which may be used are well known to those of ordinary skill in the art. For example, when formulating oral pharmaceutical compositions in powder, tablet, capsule, syrup or elixir form, any conventional pharmaceutical vehicles and excipients may be used, all as is well known in the art. The preferred form to avoid oxidation is in the form of a gelatin capsule or tablet.

For administration as an oral or nasal inhalant, known inert liquids, such as propylene glycol, may be used as vehicles. It may also be administered from a pressurized inhaler in known propellants, such as trichlorofluoromethane and dichlorodifluoromethane, with the optional presence of dispersing agents, all as is well known in the art.

Example 1: Preparation of ETA.

One mole of hydrogen per mole of eicosapentaenoic acid (C20:5ω3), hereinafter "EPA", is bubbled through pure EPA at 5° C. in the presence of a nickel catalyst. Any known nickel hydrogenation catalyst may be used for this purpose, such as Raney nickel or nickel sulfate. A partial saturation is achieved. HPLC study indicates that about 80% of the resulting material is ETA ω3; 10% is C20:3ω3; 8% is C20:1ω3; and 2% is EPA (C20:5ω3). The ETA ω3 is separated from the solution according to the same method used to separate EPA as set forth in U.S. Pat. No. 4,377,526 or by the process described in U.S. application Ser. No. 545,350 of the present inventor.

Experimental:

Eight patients suffering varying degrees of bronchial asthma were treated by means of the composition of the present invention. In all eight patients, no acute asthmatic attacks reoccurred since the start of the treatment and lung functions were improved considerably. The following eight clinical cases illustrate the effectiveness of the present invention.

1. S. S., male, age 54, suffered from bronchial asthma for five years, during which time he tried the various bronchial dilators available on the market. The products included Ventolin (albuterol sulfate) inhalation, Viarex (beclomethasone dipropionate) inhalation, and aminophylline. These provided partial relief of the symptoms. S. S. also entered psychiatric treatment which further helped him for a short while, but he still had acute asthmatic attacks, particularly during the spring season. He was treated with ETA by taking three teaspoons a day of the pure chemical orally. Within a week, he was able to give up all other medications. His lung capacity was improved considerably. For the entire two months during which he was treated with this regimen, he suffered no bronchial attacks whatsoever, and he could assume vigorous activities without shortness of breath.

2. T. E. B., female, 21 years old, suffered from bronchial spasms since the age of six. She used conventional therapeutics, such as Ventolin and Viarex, as well as cromolyn sodium (1,3bis(2-carboxychromon-5-yloxy)-2-hydroxypropane, disodium salt). Her attacks were evoked by house dust. The effect of the conventional medicines was temporary relief from symptoms but she still suffered. After being treated with three teaspoons a day of ETA, she was able to give up all of the other medicines within a week. She was able to be exposed to and to smell dust without any effect. She suffered no attacks whatsoever during the entire two months period of treatment.

3. E. Z., male, 6 years old, suffered from asthma since the age of three. Almost every night he suffered from attacks and was admitted to the emergency room three-four times a month for acute asthmatic attacks. He was given Ventolin and Asthma-18 (a proprietary combination of bronchodilators). None of these provided substantial relief. He was given ETA in the amount of 5 cc three times a day by having it added to his food, for example, poured on his salad. Within ten days all of his symptoms disappeared and he was able to discontinue all other medication. He now sleeps well and has shown no recurrence of the attacks.

4. A. A., male, age 40, heavy smoker, has suffered from bronchial asthma for the last five years. He has been treated with Ventolin and Viarex, and still had recurrent asthmatic attacks and bronchial pneumonia which was treated with antibiotics. The spasms were treated with Ventolin, and Asthma-18. After being treated with 5 cc ETA three times a day, he also was able to give up all of the medication within a week and despite continued heavy smoking, has suffered no further asthmatic attacks.

5. G. S., male, 14, has suffered from asthma since the age of 7. His asthma was not severe but asthmatic attacks were evoked by physical effort. Between attacks he had wheezing and he could not perform strenuous physical activity. He had not previously had any treatment for this problem but was limited in his activities. After receiving 5 cc ETA three times a day orally, the wheezing disappeared and he was able to resume normal physical activities without bronchial attacks.

6. Z. B., male, 52, heavy smoker, diabetic, suffered from severe asthmatic attacks and was treated with aminophylline alone which gave only partial relief. He was not able to take inhalation treatment. After taking 5 cc ETA three times a day, the symptoms disappeared although he did not quit smoking.

7. G. C., male, 38, heavy smoker, suffered from spastic bronchitis for two years. He reacted partially to Asthma-18 tablets but after treatment with 5 cc ETA three times a day, and also quitting smoking, the symptoms were relieved completely.

8. R. B., female, age 64, started suffering from spastic bronchitis four months prior to treatment. Asthma was found to be caused by hay fever. She received partial relief with Ventolin and Viarex, but upon taking 5 cc ETA three times a day, the symptoms were completely relieved.

When patients were treated during acute asthmatic attacks by inhalation of ETA in spray form in the amount of 0.05 g the attacks immediately ceased.

It is apparent that ETA is effective against asthma activity, both as treatment and as prophylaxis. It may also be used for the treatment of nasal congestion, preferably by means of an inhalator, as well as for the treatment of anaphylactic shock brought on by any reason as long as the shock is caused by the release of SRS-A.

The foregoing description of the specific embodiments will so fully reveal the general nature of the invention that others can, by applying current knowledge, readily modify and/or adapt for various applications such specific embodiments without department from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A composition for the treatment of conditions caused by excessive release of SRS-A, consisting essentially of an amount effective to inhibit relase of SRS-A of 8,11,14,17-eicosatetraenoic acid or a pharmaceutically acceptable salt or ester thereof and a pharmaceutically acceptable vehicle.

2. A composition in accordance with claim 1, wherein said pharmaceutically acceptable vehicle is chosen such as to permit administration of the composition as an inhalant.

3. A composition in accordance with claim 1, further including an anti-oxidant in an amount sufficient to substantially prevent oxidation of the unsaturations of said 8,11,14,17-eicosatetraenoic acid, salt or ester.

4. A composition in accordance with claim 3, wherein said anti-oxidant is selected such that it has both anti-oxidizing and lipoxygenase inhibiting activity.

5. A composition in accordance with claim 4, wherein said anti-oxidant is 1-phenyl-3-pyrazolidone, propyl gallate or a vitamin E.

6. A composition in accordance with claim 5, wherein said anti-oxidant is a combination of ascorbyl palmitate and γ-tocopherol.

7. A method for the treatment of conditions caused by excessive release of SRS-A, comprising administering to a patient having such a condition an amount of 8,11,14,17-eicosa-tetraenoic acid or a pharmaceutically acceptable salt of ester thereof effective to inhibit the release of SRS-A.

8. A method in accordance with claim 7, wherein said administering step is accomplished by oral or nasal inhalation.

9. A method in accordance with claim 7, wherein said administering step is accomplished orally.

10. A method in accordance with claim 1, wherein said condition is bronchial asthma.

11. A method in accordance with claim 1, wherein condition is anaphylactic shock.

12. A method in accordance with claim 1, wherein condition is nasal congestion.

13. In a pressurized container for oral or nasal inhalation administration of unit dosages of a pharmaceutical composition contained therein, said container containing an active principle and a suitable propellant, the improvement wherein said active principle is 8,11,14,17-eicosatetraenoic acid or a pharmaceutically acceptable salt or ester thereof.

* * * * *